United States Patent
Pfeifer et al.

(10) Patent No.: US 6,768,549 B1
(45) Date of Patent: Jul. 27, 2004

(54) AMPOULE ANALYZER APPARATUS

(76) Inventors: John Edward Pfeifer, 3 Great Pasture Rd., Redding, CT (US) 06896; Peter E. Rising, 146 Concourse E., Brightwaters, NY (US) 11718

( * ) Notice: Subject to any disclaimer, the term of this patent is extended or adjusted under 35 U.S.C. 154(b) by 102 days.

(21) Appl. No.: 09/590,060

(22) Filed: Jun. 8, 2000

Related U.S. Application Data

(63) Continuation-in-part of application No. 09/578,323, filed on May 24, 2000, now Pat. No. 6,493,085, and a continuation-in-part of application No. 09/557,653, filed on Apr. 25, 2000, now Pat. No. 6,444,462.

(51) Int. Cl.⁷ ............................................. G01N 21/59
(52) U.S. Cl. ...................... 356/436; 356/434; 356/442; 422/88.09
(58) Field of Search ................................ 356/432, 433, 356/434, 435, 436, 440, 441, 442, 446; 422/82.09

(56) References Cited

U.S. PATENT DOCUMENTS

| | | | |
|---|---|---|---|
| 3,877,817 A | 4/1975 | Ralston | 356/180 |
| 3,939,687 A | 2/1976 | Waldron | 73/1 |
| 3,994,590 A | 11/1976 | Di Martini | 356/178 |
| 4,027,979 A | 6/1977 | Komarniski | 356/180 |
| 4,309,112 A * | 1/1982 | Ashley et al. | 356/436 |
| 4,392,746 A | 7/1983 | Rook et al. | 356/409 |
| 4,475,823 A | 10/1984 | Stone | 374/1 |
| 5,013,155 A * | 5/1991 | Rybak | 356/408 |
| 5,144,814 A | 9/1992 | Gaudette | 62/225 |
| 5,307,144 A | 4/1994 | Hiroshi et al. | 356/244 |
| 5,345,064 A | 9/1994 | Hesse | 219/505 |
| 5,677,134 A | 10/1997 | Hayashi et al. | 435/7.4 |
| 5,703,342 A | 12/1997 | Hoffmann et al. | 219/497 |
| 5,770,389 A | 6/1998 | Ching et al. | 435/7.92 |
| 5,903,346 A | 5/1999 | Rinke et al. | 356/320 |
| 5,959,738 A | 9/1999 | Hafeman et al. | 356/440 |
| 6,004,029 A | 12/1999 | Moslehi et al. | 374/1 |
| 6,010,243 A | 1/2000 | Hessler et al. | 374/1 |
| 6,172,759 B1 * | 1/2001 | Goldstein | 356/437 |
| 6,306,577 B1 * | 10/2001 | Tamura et al. | 422/82.09 |

* cited by examiner

*Primary Examiner*—Richard A. Rosenberger
(74) *Attorney, Agent, or Firm*—Gordon & Jacobson, P.C.

(57) ABSTRACT

An analyzer apparatus includes a receptacle for an ampoule, an analysis system, an incubator, and a master control. The analysis system includes a light source and a photodetector positioned such that the light from the light source passes through the receptacle. The master control includes a display, a timer, and a memory provided with a look-up table. During operation, an ampoule containing a sample and an indicator which changes color when a certain level of biological activity is present in the sample is placed within the receptacles. The analysis system is operated to transmit light at the predetermined wavelength through the ampoule to the detector, and a maximum amount of light passing through the ampoule is logged. The incubator is operated to heat the receptacle and the ampoule therein to a desired test temperature and the timer is started. The analysis system periodically transmits light through the ampoule. Increased biological activity in the ampoule causes a color change in the indicator which reduces light transmission through the ampoule. When the light detected is reduced relative to the light transmitted by a predetermined percentage of the maximum amount of light, the master control signals that the test is complete. Based on the amount of time required for this to occur, the master control determines from the look-up table the bacterial content in the sample at the start of the test.

7 Claims, 5 Drawing Sheets

```
PLACE          SELECT
AMPOULE   →    AMPOULE
IN             TYPE
RECEPTACLE
   100         102
```

- 106: ACTIVATE LIGHT ANALYSIS SYSTEM TO TRANSMIT LIGHT THROUGH AMPOULE
- 108: LOG LIGHT LEVEL
- 104: ACTIVATE INCUBATION SYSTEM
- 114: READ TEMPERATURE

AMPOULE ANALYZER APPARATUS

This application is a continuation-in-part of both U.S. Ser. No. 09/557,653, filed Apr. 25, 2000, now U.S. Pat. No. 6,444,462 and U.S. Ser. No. 09/578,323, entitled "Light Analyzer Apparatus" and filed May 24, 2000, now U.S. Pat. No. 6,493,085 which are both hereby incorporated by reference herein in their entireties.

BACKGROUND OF THE INVENTION

1. Field of the Invention

This invention relates broadly to analytical instruments. More particularly, this invention relates to an analyzer apparatus for determining when a photometric change occurs in a sample, and relating the change to a condition of the sample at a previous time.

2. State of the Art

Water quality, and particularly bacterial content in water is of great concern. Municipalities perform periodic checks of water quality to ensure that water reserves are safe. Recently, home monitoring of water quality has become popular.

A number of products are available for testing water quality. One variety of product is an ampoule which is a sealed evacuated vial containing a powdered nutrient for microbes and an indicator which changes color when the concentration of microbes reaches a specific high level. One such ampoule is shown in U.S. Pat. No. 5,935,799 to Isbister. In use, a user inverts the ampoule in a cup of sample water and breaks off a scored tip of the ampoule. The vacuum in the ampoule causes the ampoule to fill with sample water. The ampoule is then shaken to mix the powdered nutrient and indicator with the water. Finally, the ampoule must be maintained at a constant temperature, e.g., 34° C., for a relatively long period of time, e.g., up to 12 hours. One manner often suggested by manufacturers of the ampoules for maintaining proper temperature is for the user to place the ampoule in a shirt pocket of the user, since the shirt pocket is approximately at the desired temperature. Periodically, e.g., every thirty minutes, the user must look for the indicator to change color by holding the ampoule up the light and comparing the observed color against a printed chart. When the color change is observed, the elapsed time is recorded and a second chart is used to look up the number of microbes that were in the original sample water based upon the recorded time.

The determination of the number of microbes is based on the fact that microbes multiply by binary fission. The number of microbes in the original sample may therefore be determined by reference to an exponential chart and the recorded time.

While this type of analytical product is useful, it has several drawbacks. One problem is the requirement to hold the ampoule in a shirt pocket for incubation. Another problem is that the accuracy is questionable, as human judgment is required to read the color at the end point.

Several apparatus have been disclosed to test samples, but they do not address the testing requirements for the above described ampoules. For example, U.S. Pat. No. 5,013,155 to Rybak discloses an apparatus which determines a specific color of a sample in a vial received in a receptacle in the apparatus. The device uses two light sources, each of a different color, which are alternatingly pulsed, and respective photodetectors. The results are interpolated along with signals present when no light is emitted, to identify the specific color of the test sample. The Rybak apparatus requires a vial of clear distilled water to calibrate the instrument. In addition, the device is not adapted for heating test vials at a constant temperature.

U.S. Pat. No. 5,959,738 to Hafeman et al. uses either a single light source capable of operating at multiple wavelengths, or multiple and different wavelength light sources. A relationship is determined between the light absorption properties of a liquid sample (solvent and analyte) and the optical pathlength of the liquid sample to calculate a concentration of an analyte in a solvent of the sample. The device is not capable of determining when a change occurs in the contents of an ampoule when the contents of an ampoule are already known.

Therefore, what is required is a device adapted to determine biological activity as a result of a decrease in light passage through a sample over time.

SUMMARY OF THE INVENTION

It is therefore an object of the invention to provide a apparatus for determining when a particular change in the contents of an ampoule occurs via photometric measurements.

It is another object of the invention to use a single wavelength light source which functions as both a reference beam and a measuring beam.

It is a further object of the invention to provide an apparatus which centralizes all componentry of the light emission and detection system.

It is an additional object of the invention to provide an apparatus which is substantially free from error due to ambient light.

It is a also an object of the invention to provide an apparatus which determines at time at which a targeted photometric change occurs in an sample, and relating the targeted change to a condition of the sample at a previous time.

It is yet another object of the invention to provide an apparatus which maintains ampoules at a desired temperature.

It is yet a further object of the invention to provide a portable and relatively low cost apparatus for heating and analyzing changes in the contents of an ampoule.

In accord with these objects, which will be discussed in detail below, an ampoule analyzer apparatus is provided which includes a housing having at least one receptacle (or nest) for an ampoule, a cover for substantially preventing ambient temperature and light from affecting each receptacle, a light analysis system, an incubation system, and a master control system.

The light analysis system includes, for each receptacle, at least one light source and a photodetector positioned such that the light from the light source passes through the receptacle (and thereby the ampoule and its contents) prior to entering the photodetector. The light source is chosen to deliver a predetermined wavelength of light such that the color change of the contents of the ampoule causes reduction in the intensity of the light transmitted through the contents of the ampoule.

The incubation system includes, for each receptacle, a heating element which rapidly heats the receptacle to a desired temperature and a temperature sensor which senses the temperature of the receptacle. Each receptacle is preferably insulated to prevent unintended heating of neighboring receptacles of the apparatus.

The master control system permits user input, operates the light analysis system and the incubation system. In addition, the master control system includes a timer, and a memory provided with a look-up table relating the type of test, the time to test completion, and the associated bacterial count at the start of the test. A user-readable display for the output of the results, e.g., the bacterial count at time zero, is also provided.

During operation, an ampoule containing a water sample and a reagent which causes the sample to change color when a certain level of biological activity is present in the sample is placed within one of the receptacles. The light analysis system is operated to transmit light at the predetermined wavelength through the ampoule (either axially or transversely) to the detector, and a maximum amount (intensity) of light passing through the ampoule is determined. The incubation system is also operated to heat the receptacle and the ampoule therein to a desired test temperature and the timer is started. The light analysis system periodically transmits light through the ampoule. Increased biological activity in the sample causes a color change to the indicator which reduces light transmission through the ampoule. When the light detected at the detector is reduced relative to the light transmitted by a predetermined percentage of the maximum amount of light, the master control system signals that the test is complete. Based on the amount of time required for this to occur, the master control system determines from the look-up table the bacterial content in the sample at the beginning of the test and displays the results on the display.

The apparatus may include a large number of receptacles suitable for laboratory use or may include fewer or one receptacle suitable for home or portable use.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
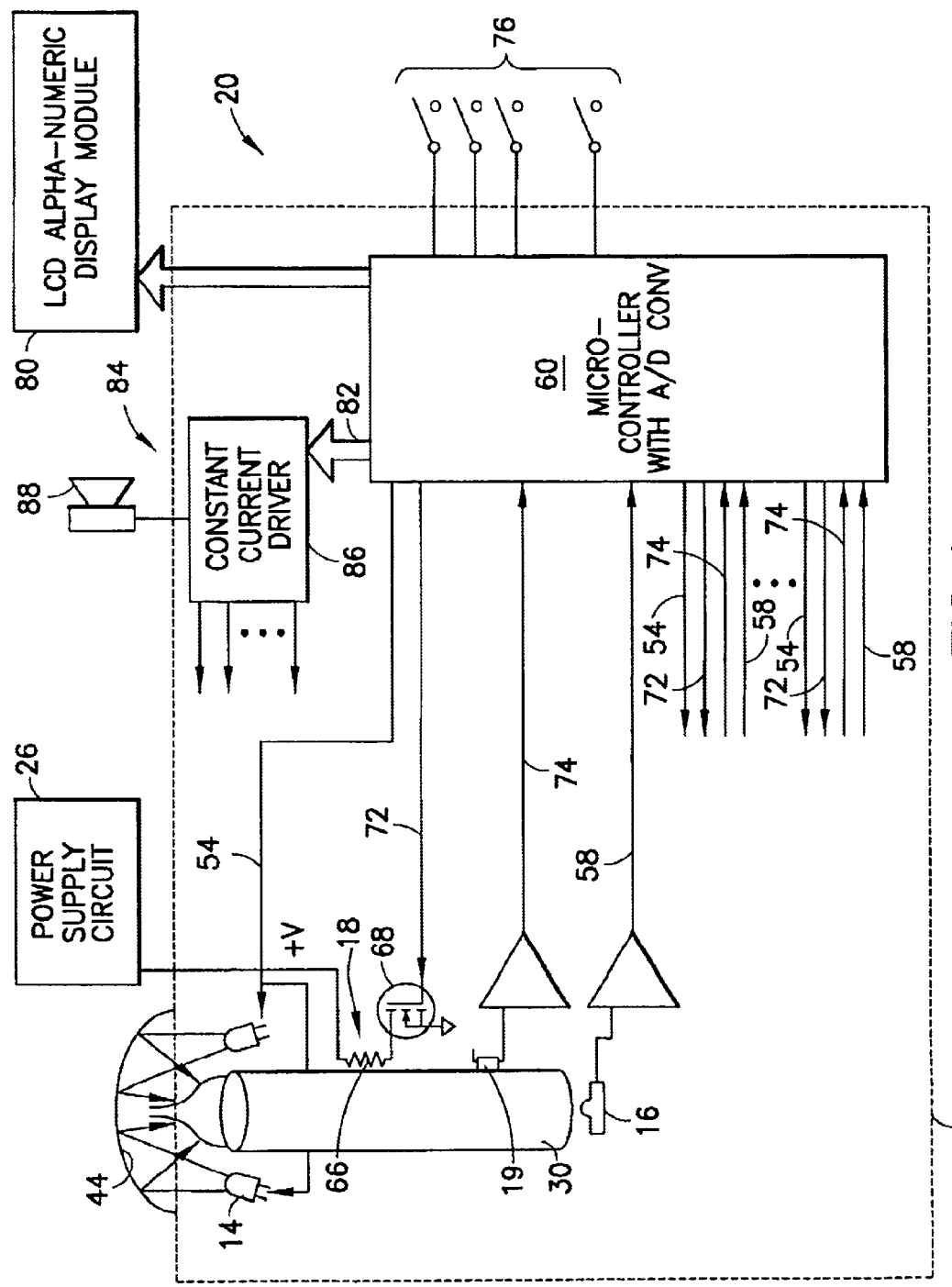
FIG. 1 is a schematic circuit diagram of the apparatus of the invention.

Turning now to FIGS. 1 through 4, an ampoule analyzer apparatus 10 according to the invention includes a housing 12 having a light analysis system (a light source 14 and an optical detector 16, collectively ), an incubation system (a heating element 18 and a sensor chip 19, collectively), and a master control system 20, each of which is discussed in detail below. The housing 12 also includes a battery 24 and associated circuitry 26 to power the various systems. A preferred battery 24 and circuitry 26 are disclosed in previously incorporated U.S. Ser. No. 09/578,323.

Six receptacles (nests) 30, each for receiving an ampoule 32, are provided in the housing. The housing 12 is also preferably provided with a planar lower surface 34 which is adapted to seat the housing on a planar surface, and a storage area 36 for storing ampoules or other items. A lid 38 movable between closed and open (broken lines) positions covers and uncovers the receptacles 30, the storage area 36, and other exposed components to protect them from the elements, and to facilitate transportation of the apparatus.

A receptacle cover 40 in an open position provides access to the receptacles 30 and in a closed position 40a substantially individually seals each receptacle to prevent ambient light from affecting the receptacle. The receptacle cover 40 preferably includes a plurality of concave portions 42 each having a diffuse reflective interior surface 44 which reflects and distributes light from a light source, discussed below, through the receptacles.

Figure 2:
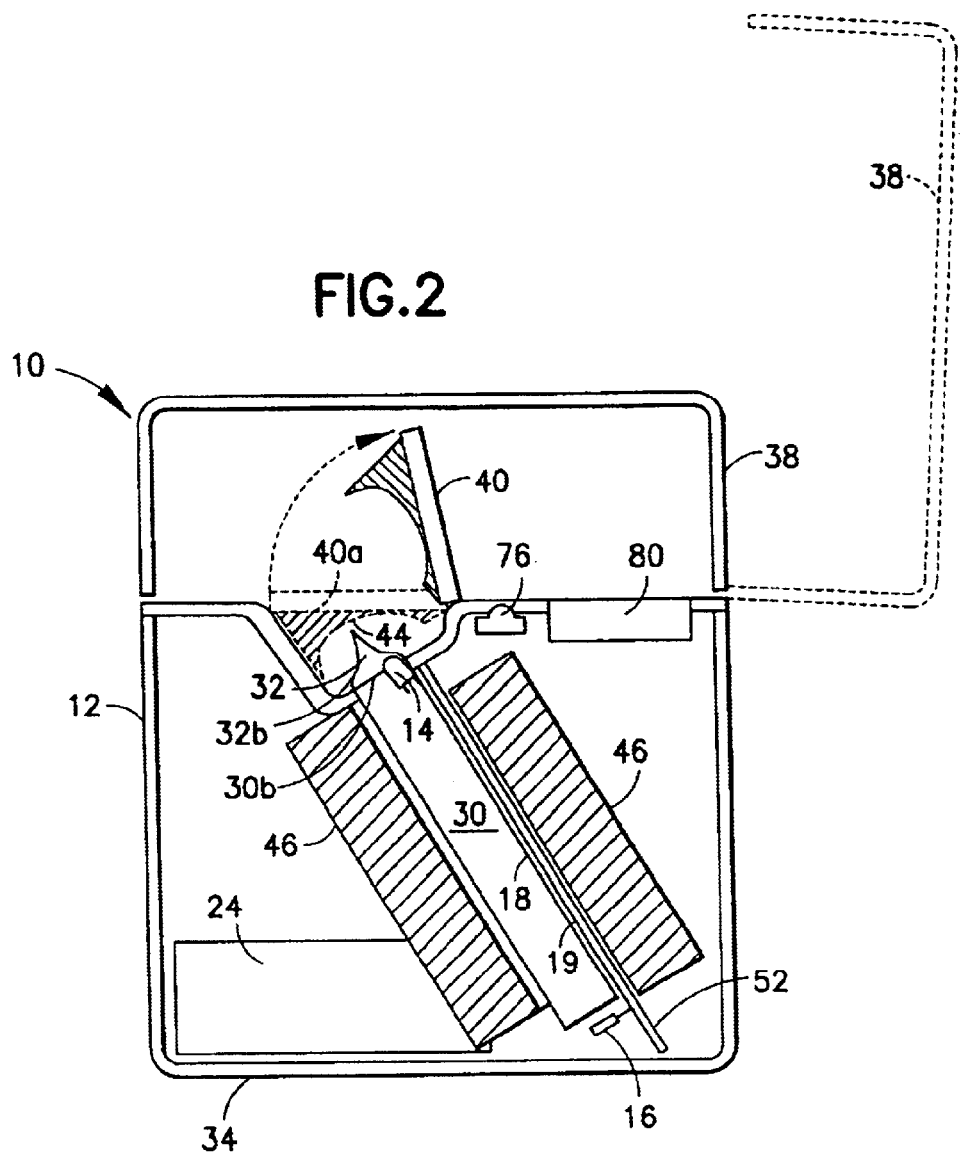
FIG. 2 is a partial side view of the apparatus of the invention showing the case lid in open and closed positions.
Figure 3:
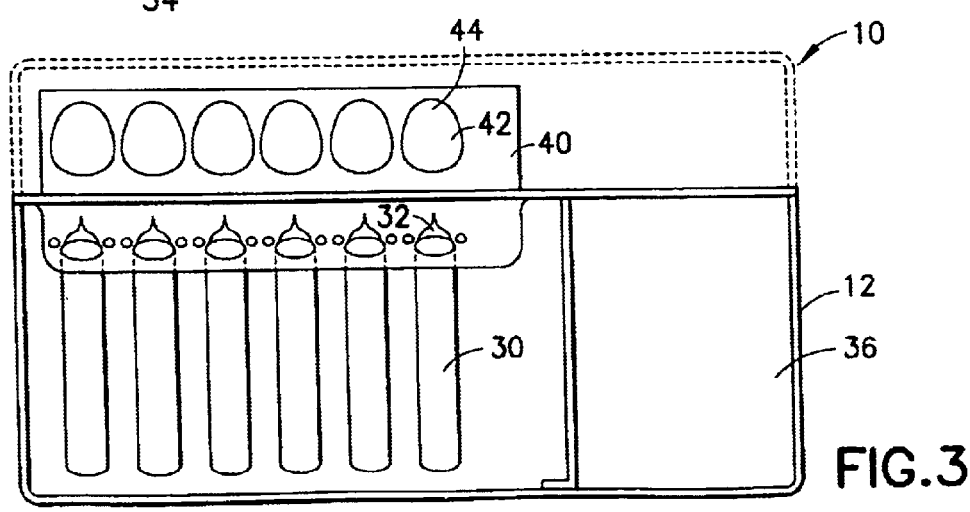
FIG. 3 is a partial front view of the analyzer apparatus of the invention.
Figure 4:
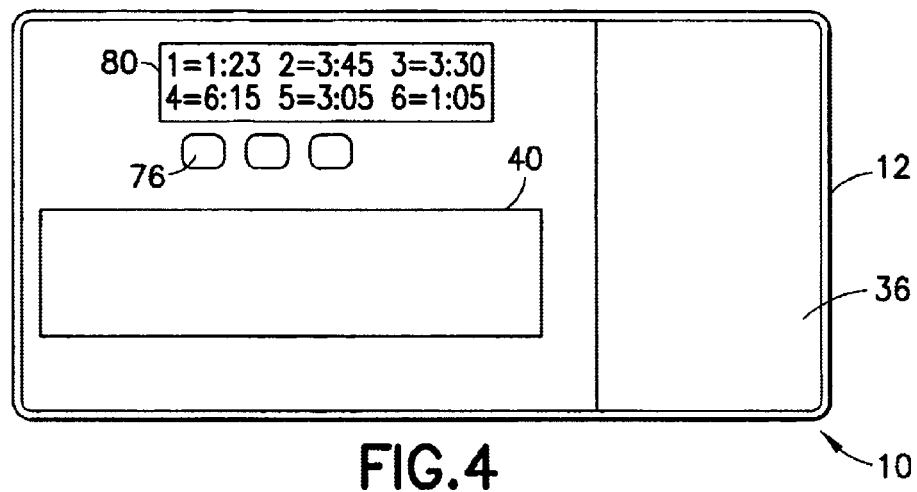
FIG. 4 is a top view of the apparatus of the invention without the case lid.
Figures 5, 6:
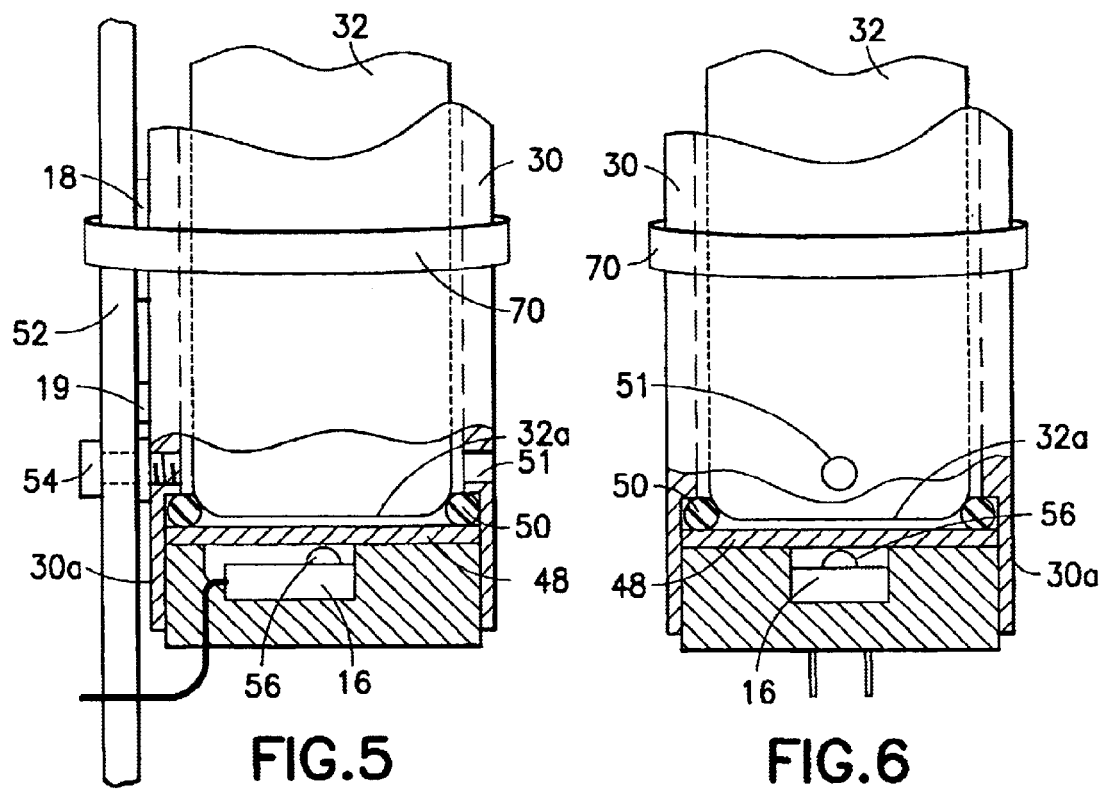
FIG. 5 is a side view of an ampoule receptacle according to the invention.
FIG. 6 is a front view of an ampoule receptacle according to the invention.

Each receptacle 30 is an opaque tube; e.g., metal or plastic, approximately 0.5–0.625 inch in diameter, and preferably approximately four inches in length. The receptacles 30 are individually surrounded by a thermally insulative foam 46 to maintain the temperature of the receptacle during heating by the incubation system, as described below. Turning to FIGS. 5 and 6, a transparent preferably cleanable disk 48, preferably glass or polycarbonate, is provided near a lower end 30a of the receptacle. The closed end 32a of the ampoule 32 is provided near the disk 48, with the open end 32b of the ampoule at the upper end 30b of the receptacle (FIG. 2). An O-ring 50 provides a watertight seal between the disk 48 and the interior surface of the receptacle 30. A weep hole 51 is provided in the receptacle adjacent but above the location of the disk 48 to permit any water, test solution, or cleaning/sterilization solution which may drip into the receptacle 30 to drain therefrom.

Referring to FIGS. 1, 2 and 5, the receptacles 30 are attached to a printed circuit board (PCB) 52, e.g., by screws 54, preferably such that a longitudinal axis of each receptacle runs parallel to the plane of the PCB. Each receptacle 30 is provided with the light source 14 and the optical detector 16 which are each electrically coupled to a microcontroller 60 of the master controller 20. Both the light source 14 and optical detector 16 are also preferably physically coupled to the PCB 52. The light source 14 includes one or more LEDs adapted to emit light at a predetermined wavelength into the receptacle 30 when receiving a signal 54 from the microcontroller 60. According to a preferred embodiment of the invention, the light source 14 is a plurality of LEDs coupled to the PCB 52 in an orientation such that they preferably direct light into the reflective interior surface 44 of the associated portion 42 of the cover 40 of housing 12. The reflective surface 44 scatters the light of the LEDs 14 substantially axially through the ampoule 32 in the receptacle 30 and toward the detector 16 located at the lower end 30a of the receptacle (FIGS. 1 and 2). A preferably hemispherical lens 56 is preferably provided to gather the scattered light and channel the light transmitted through the ampoule 32 toward the detector 16 (FIGS. 5 and 6). The optical detector 16 provides a return signal 58 to the microcontroller 60. The return signal 58 is amplified and filtered with a time constant to null out any short term changes which may be caused by bubbles breaking at the top surface. The analog return signal is provided to an analog to digital converter associated with the microcontroller 60.

The receptacles 30 are preferably provided at an oblique, non-perpendicular angle relative to both the vertical and the horizontal, e.g., 30° to 45° off vertical, by angling the receptacles relative to the lower surface 34 of the housing 12. The angle of the receptacles 30 facilitates axial light transmission through the ampoules by preventing sediment from accumulating on the entire bottom of the ampoule and thereby blocking all light paths between the reflective surface 44 and the optical detector 16. Moreover, the ampoules are preferably provided with a stirring rod which will settle outside a direct axial light path when the receptacles are angled. As the receptacles 30 are preferably coupled to the PCB 52, one preferred manner of providing the angle is to orient the entire PCB at the desired angle relative to vertical within the housing 12. The above described configuration of the light source 14, optical detector 16, and orientation of the receptacles 30 provides a system in which all componentry is preferably provided at or below the level of the top 32b of the ampoule 32. This configuration facilitates sealing the receptacles 30 from ambient light, with the reflective surface 44 of the cover 40 providing the redirection of the light into the required path through the receptacle and ampoule. In addition, as the cover 40 is capable of reflecting the light, the need for separate reflectors is obviated and a system with fewer components, and therefore lower cost, is provided.

As briefly discussed above, the light source 14, preferably a plurality of LEDs, is adapted to emit light at a predetermined wavelength. Optionally, the LEDs may emit light at different wavelengths, and then, depending upon which wavelength is desired, the LED which produces light at that wavelength is selected. In addition, the master control system 20 may be operated to cause the microcontroller 60 to signal all the LEDs of the light source 14 to emit light constantly, alternatingly, or to be pulsed.

Still referring to FIGS. 1, 2 and 5, the incubation system includes the heating element 18 adapted to heat the receptacle 30 and a temperature sensor chip 19 in contact with the receptacle 30 for determining the temperature thereof. The heating element 18 includes a pack of heating resistors 66 and a driver FET (field effect transistor) 68 which is also coupled to the microcontroller 60 of the master control system 20. The temperature sensor chip 19 is preferably a silicon device which produces a voltage related to a sensed temperature. The sensor chip 19 is preferably held tightly against the receptacle 30 to accurately sense the temperature of the receptacle. Preferably, one of the screws 54 provides a heat conductive path from the receptacle 30 to the temperature sensor 19, and a tie wrap 70 preferably sandwiches the heating resistors 66 between the PCB 42 and the receptacle 14 (FIG. 5). The incubation system is preferably calibrated to quickly and accurately heat the receptacle (and consequently the ampoule provided therein) to a desired temperature. Calibration of the incubation system, as well as software control and associated control signals 72, 74 to and from the heating element 18 and sensor chip 19 to bring and maintain the receptacle 30 to a desired temperature, are discussed in detail in co-pending and previously incorporated U.S. Ser. No. 09/557,653.

Referring back to FIG. 1, the master control system 20 of the analyzer apparatus 10 includes the microcontroller 60, a timer, and a control button 76 permitting user input and operation. In addition, the master controller 20, through the microcontroller 60 operates the light analysis system 14, 16 and the incubation system 18, 19, and provides information to a user-readable display 80 and a signal 82 to an audio output 84 (comprised of a driver chip 86 and a sound transducer 88) for the output of the results of testing with the analyzer.

The ampoules 32 used in the apparatus, the operation of which is discussed below, contain a water sample and a reagent which changes color (a color indicator) when a certain level of biological activity (total microbial count, *E. Coli*, Coliform, etc.) is present. Numerous such reagents are disclosed in detail in U.S. Pat. No. 4,204,037 to Frosch et al., U.S. Pat. No. 4,332,769 to Rampy et al., U.S. Pat. No. 5,212,876 to Turner et al., and U.S. Pat. No. 5,935,799 to Isbister, each of which is hereby incorporated by reference herein in its entirety. For each type of ampoule, an ampoule calibration is performed to determine the percentage of light reduction which occurs at a particular light wavelength when the indicator turns sufficient color to indicate an end of test. For example, an ampoule containing a reagent used to indicate the total microbial count in a sample has been shown to reduce light transmission to seventy-five percent of the maximum light transmission through a sample by its color change at test end. The types of ampoules, and the predetermined amount of light transmission reduction at particular light wavelengths required to indicate test completion is stored in a memory of the master control system 20.

Figure 7B:
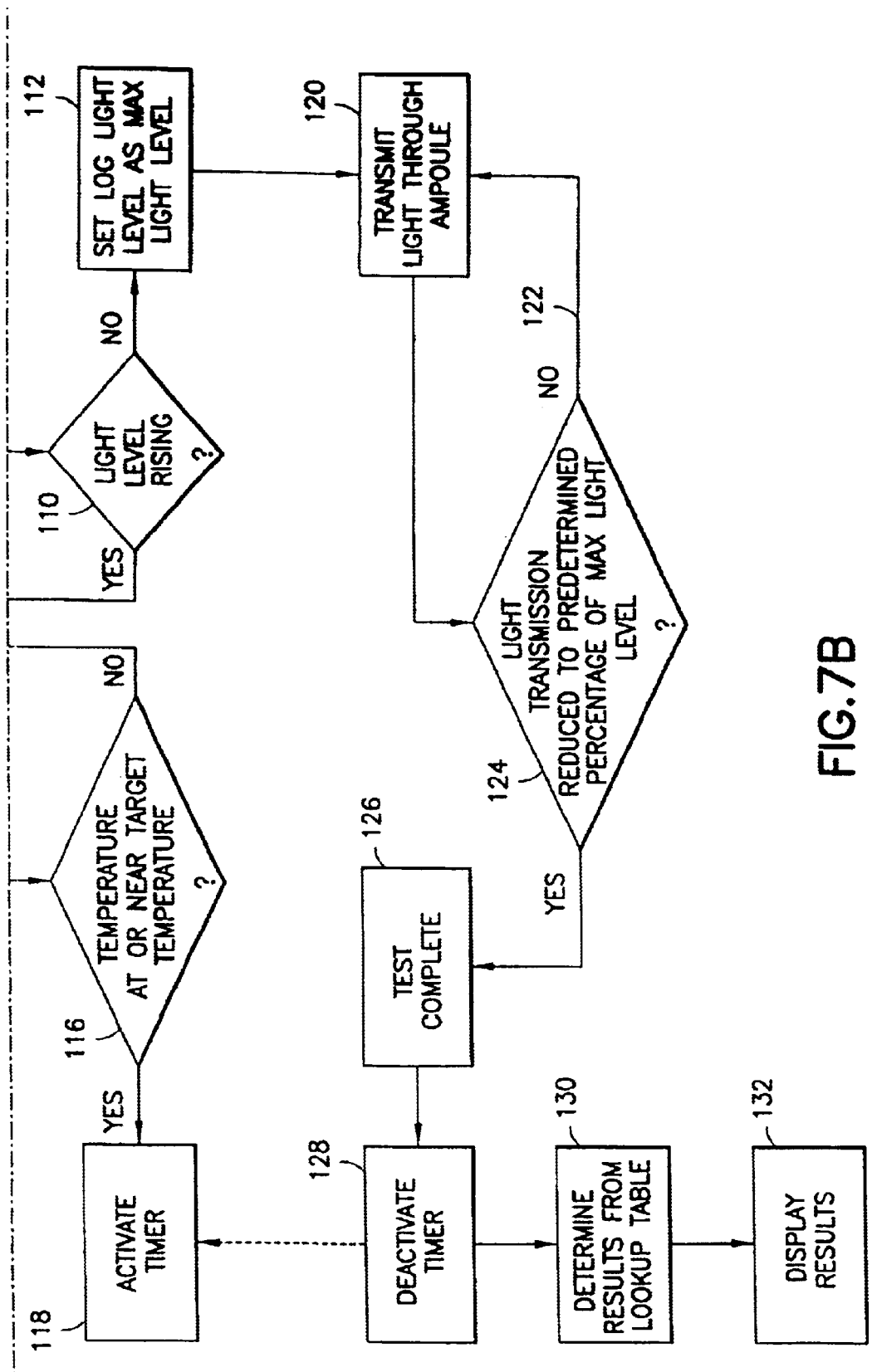
FIG. 7 is a flow chart illustrating the operation of the apparatus of the invention.

Turning now to FIGS. 1, 2 and 7, in operation, an ampoule 32 is placed at 100 in a receptacle 30 of the apparatus 10. The master controller is operated at 102 to indicate a type of ampoule; i.e., reagent and test being performed. The incubation system is then activated at 104 to begin bringing the ampoule to the desired test temperature, e.g., 34° C., which increases the biological activity in the sample. In addition, the light analysis system is operated at 106 to transmit light at a predetermined wavelength, selected for the ampoule under test, through the ampoule to the detector. The light level (intensity) measured by the photodetector and logged at 108 at regular intervals, e.g., every minute. The light transmission through the ampoule may initially increase, as small bubbles rise out and larger bubbles break at the surface. Once the light level stops rising at 110, the light level is logged and indicated at 112 as the maximum amount of light transmission that can be expected through the ampoule. This self-calibration test is carried out for each ampoule in each receptacle.

Meanwhile, the temperature sensor chip 19 reads at 114 the temperature of the receptacle. When the chip 19 senses at 116 that the temperature of the ampoule is close to the target temperature, e.g., within one to five degrees Celsius of the target temperature, the timer is activated at 118 to begin counting time until the indicator changes color sufficient to reduce the light transmission to a predetermined percentage of the maximum.

The detection of the indicator color changes is enhanced by the choice of the light source wavelength. For example, an ampoule for testing the total microbial count turns red as the microbial count rises. As such, 565 nm green LEDs are preferred for light transmission through the ampoule in such a test, as the red reagent indicator effectively limits transmission of 565 nm light therethrough. The LED color (i.e., light wavelength) is selected by the master control system 20 based upon the type of ampoule selected. In addition, as the sample may contain some degree of turbidity; i.e., debris or small air bubbles that will scatter light, it has been found that the preferred green wavelength is relatively insensitive to the light scattering effects of turbidity. Furthermore, as stated above, the effect of turbidity is also limited by the initial self-calibration.

Periodically, e.g., every minute to every hour, light is transmitted at 120 by the light source through the ampoule. This continues at 122 until the color change in the reagent is sufficient to reduce at 124 light transmission of the selected wavelength by a predetermined amount and indicates the test is complete at 126. The timer is then stopped at 128. It is noted that at no time during the test is a human visual comparison between the color of the contents of the ampoule and a reference required. Based on the amount of time required for test completion, the master control system 20 determines at 130 from a look-up table stored in memory the bacterial content in the sample at the beginning of the test and displays at 132 the results on the display 80. The result is preferably displayed until a new test is started or the power switch is turned off.

According to a second embodiment of the apparatus, substantially similar to the first, the light source and light detector are located on opposite sides of the receptacle rather than at the ends thereof. As such, light is transmitted transaxially across the receptacle and through the ampoule. The apparatus of the second embodiment is used in substantially the same manner as the first embodiment. However, it is noted that the samples in some ampoules under test may contain microbes that form various films at different levels within the ampoule; i.e., a stratification of the sample. As such, the axial embodiment is preferred as it eliminates any artifacts caused by stratified layers. In addition, the axial measurement embodiment permits the light to be transmitted through about four inches of the sample water, as, opposed to about 0.5 inch of water with the transaxial mode. The larger amount of sample water provides a proportionally denser color change when the indicator changes color.

There have been described and illustrated herein embodiments of an analyzer apparatus. While particular embodiments of the invention have been described, it is not intended that the invention be limited thereto, as it is intended that the invention be as broad in scope as the art will allow and that the specification be read likewise. Thus, while a battery and associated circuitry have been disclosed, it will be appreciated that other power systems may be used as well. In addition, while a particular calibration system has been disclosed for the incubation system, other incubator calibration systems may be used as well. In addition, while the temperature sensor is described as producing a voltage proportional to a sensed temperature, it may alternatively produce a voltage inversely proportional to a sensed voltage, each of which is considered 'proportional' in the claims. Also, while a field effect transistor is preferred as part of the heating element, other transistors, such as a switching transistor, may also be used. In addition, while the receptacles are preferably made entirely from a heat conductive material, it will be appreciated that only elements of the receptacle need be made from a heat conductive material. For example, the receptacle may alternatively include a coiled heating element which resides in the interior of the receptacle and which is in contact with the heating element. Furthermore, while the apparatus has been described using ampoules and reagents and light wavelengths suitable for testing for total microbial count in a sample, it will be appreciated that other ampoules testing for E. coli, Coliforms, and other biological and chemical presences can also be used. Furthermore, while a preferred incubation temperature of 34° C. is disclosed, it will be appreciated that other temperature about 34° C. are suitable, e.g., 32° C.–37° C., for a total microbial test, and that other temperatures may be preferred for other tests. In addition, while the apparatus has been described with six independently operable receptacles, the apparatus may include a larger number (e.g., 24 to 36) of receptacles such that it is suitable for laboratory use or may include fewer or one receptacle suitable for home or portable use. It will therefore be appreciated by those skilled in the art that yet other modifications could be made to the provided invention without deviating from its spirit and scope as claimed.

What is claimed is:

1. A method of analyzing contents of an ampoule, the ampoule containing a sample and a reagent which changes color when a predetermined level of biological activity is present in the sample, said method comprising:
   a) recording a maximum intensity of light transmitted through said ampoule by transmitting light at a predetermined wavelength at regular intervals and identifying when said intensity of light transmitted through said ampoule stops increasing;
   b) identifying a first time;
   c) transmitting light at the predetermined wavelength through said ampoule;
   d) identifying an end time relative to said first time at which an intensity of said light transmitted at said predetermined wavelength through the ampoule is at a predetermined percentage of said maximum intensity of light; and
   e) automatically determining from said end time a level of biological activity present in the sample at said first time.

2. A method according to claim 1, wherein:
   said predetermined wavelength is 565 nm.

3. A method according to claim 1, wherein:
   said transmitting light transmits light axially through said ampoule.

4. A method according to claim 1, wherein:
   said automatically determining includes referencing a look-up table in a memory.

5. A method according to claim 1, further comprising:
   g) heating the ampoule to or near a target temperature.

6. A method according to claim 5, wherein:
   said target temperature is approximately between 32 and 37° C.

7. A method according to claim 5, wherein:
   said first time is set when said ampoule is heated to or near said target temperature.

* * * * *